(12) United States Patent
Whittle et al.

(10) Patent No.: US 6,730,330 B2
(45) Date of Patent: May 4, 2004

(54) PHARMACEUTICAL FORMULATIONS

(75) Inventors: Brian A. Whittle, Hornsea (GB); Geoffrey W. Guy, Piddletrenthide (GB)

(73) Assignee: GW Pharma Limited, Wiltshire (GB)

( * ) Notice: Subject to any disclaimer, the term of this patent is extended or adjusted under 35 U.S.C. 154(b) by 0 days.

(21) Appl. No.: 09/827,158

(22) Filed: Apr. 5, 2001

(65) Prior Publication Data

US 2002/0136752 A1 Sep. 26, 2002

Related U.S. Application Data

(60) Provisional application No. 60/280,044, filed on Mar. 30, 2001.

(51) Int. Cl.[7] .................. A01N 65/00; A61K 35/78
(52) U.S. Cl. ........................... 424/725; 424/435
(58) Field of Search ................ 449/448, 449, 449/450, 260; 514/937

(56) References Cited

U.S. PATENT DOCUMENTS

| 3,428,728 A | 2/1969 | Lowey | |
|---|---|---|---|
| 3,560,625 A | 2/1971 | Costello et al. | |
| 4,464,378 A | * 8/1984 | Hussain | 424/260 |
| 5,462,749 A | 10/1995 | Rencher | |
| 5,472,706 A | * 12/1995 | Friedman et al. | 424/450 |
| 5,719,197 A | * 2/1998 | Kanios et al. | 514/772.6 |
| 5,891,469 A | * 4/1999 | Amselem | 424/451 |
| 6,057,289 A | * 5/2000 | Mulye | 514/11 |

FOREIGN PATENT DOCUMENTS

| WO | WO 95/05163 A1 | 2/1995 |
|---|---|---|
| WO | WO 95 25504 A | 9/1995 |
| WO | WO 95/34286 A1 | 12/1995 |
| WO | WO 01 66089 A | 9/2001 |

OTHER PUBLICATIONS

Gershanik and Benita, *Proc. 26rh Int. Symp. Control. Rel. Bioact. Mater.* 913–914 (1999).
Gershanik and Benita, *Pharmaceutical Devel. and Technol.* 1(2): 147–157 (1996).

* cited by examiner

Primary Examiner—Thurman K. Page
Assistant Examiner—Micah-Paul Young
(74) Attorney, Agent, or Firm—Wolf, Greenfield & Sacks, P.C.

(57) ABSTRACT

The invention relates to pharmaceutical formulations for use in the administration of medicaments, in particular lipophilic medicaments, via mucosal surfaces.

16 Claims, 1 Drawing Sheet

Figure 1:
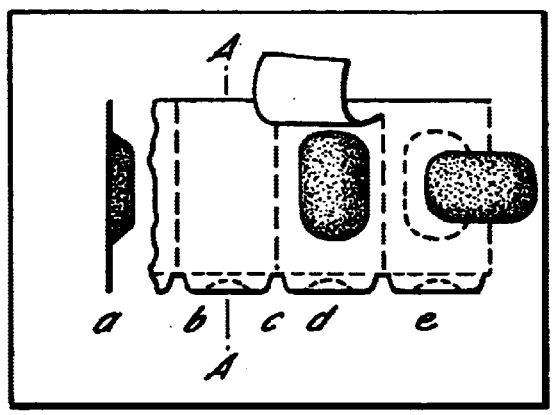

PRODUCT IN PLACE.

PRODUCT AND
PACKAGING x ½.
a CROSS SECTION AT A-A.
b SEALED PRODUCT IN
  FOIL PACKAGING.
c PERFORATION.
d OPENED PACK.
e PRODUCT READY FOR USE.

METHOD OF APPLICATION
TO MAXILLARY FOSSA.

PRODUCT IN PLACE.

AREA OF MUCOSA STAINED
AFTER 1 MINUTE.

PHARMACEUTICAL FORMULATIONS

RELATED APPLICATIONS

This application claims priority under 35 U.S.C. §119 from U.S. provisional application 60/280,044 entitled PHARMACEUTICAL FORMULATIONS, serial number not yet assigned, filed Mar. 30, 2001.

The invention relates to pharmaceutical formulations for use in the administration of medicaments, in particular lipophilic medicaments, via mucosal surfaces.

Medicaments taken by mouth and swallowed are absorbed first into the blood perfusing the gastrointestinal tract. The venous drainage from the GI tract is into the blood perfusing the liver. This means that medicaments absorbed from the lumen of gastrointestinal tract are immediately presented to the liver—the major detoxifying organ of the body. In addition to protecting the organism from ingested toxins, the liver also metabolises medicaments which are treated in the same way. Blood from the liver then returns to the left side of the heart via the hepatic portal vein and reaches the rest of the systemic circulation. This first pass through the liver may result in the removal of substantial proportion of an ingested medicament. The first pass effect is more pronounced for some drugs than others; in the case of cannabinoids more than 90% of an ingested dose is removed during the first pass.

Certain areas of the alimentary canal have a venous drainage which does not involve a first pass through the liver. These areas (the mucous membrane of the buccal cavity, under the tongue and the nasopharynx,, and also the rectum) drain directly into the left side of the heart. The avoidance of the first pass effect is the rationale for the use of buccal, nasal and sublingual formations, and also suppositories. Each of these types of formulation has advantages and disadvantages, as follows:

Suppositories are subject to hygiene and patient compliance restrictions.

Formulations intended for administration to the nasal mucosae may cause pain or reflex sneezing, and in extreme cases cause irritation and damage to the nasal mucosae.

Sublingual formulations may stimulate the flow of saliva and it is difficult for patients to avoid swallowing when substantial amount of saliva are produced. Buccal formulations may be subject to the same limitations.

Both sublingual and buccal formulations depend on the efficient transfer of medicament from a hydrophilic vehicle to the mucous membrane of the sublingual or buccal mucosae. Transfer of medicament through the interstices between or through epithelial cells is governed principally by the lipid solubility of the medicament. Where a drug is water insoluble this is a further barrier to absorption from the sublingual area. There are therefore physical and biological limitations on the therapeutic usefulness of lipophilic medicaments such as, for example, cannabis and cannabinoids given by mouth and swallowed.

The present invention relates to formulations which are particularly suitable for use for administration of lipophilic medicaments via a mucosal surface such as, for example, the sublingual mucosa.

Therefore, in accordance with a first aspect of the invention there is provided a pharmaceutical formulation for use in administration of a lipophilic medicament via a mucosal surface, the formulation comprising at least one lipophilic medicament and a matrix comprising at least one self emulsifying agent which when hydrated forms an emulsion containing the lipophilic medicament which is capable of adhering reversibly to a mucosal surface and allowing controlled release of the medicament.

By direct experiment it has been shown that lipophilic medicaments can be effectively brought into intimate contact with the absorptive mucous membrane when they are formulated in a self-emulsifying matrix.

The matrix may further comprise one or more viscolising agents (agents which increase viscosity). The inclusion of viscolising agents which are susceptible to enzymatic degradation into the matrix produces an in situ mass which has the characteristics for optimising absorption from the buccal cavity and sublingual mucosae. Surprisingly formulations made in this way do not produce reflex salivation as salivary secretion is attracted into the dose unit, and forms an in situ emulsified hydrogel. Further, the mass so formed adheres to and forms a layer on the buccal and/ox sublingual mucosae, and thereby provides a controlled release formulation.

The examples illustrate the way in which sublingual and buccal formulations can be made from intractable, lipophilic drug substances such as cannabinoids. However, the utility of the invention is not limited to this class of active ingredient and Table 1 lists some of the active ingredients by reference to class, and individual drugs which can be formulated according to the present invention.

A wide variety of hydrophilic viscolising agents have been used in pharmaceutical preparations and it is known that gels formed by hydration of these substances may have a surface electrical charge. Table 2 lists some (but without restriction to the scope of the invention) agents, which have this property, and indicates those that have received regulatory approval in preparations intended for oral administration the table also indicates the sign of the surface charge, where it is known.

Surprisingly it has been found that by selective admixture of materials producing gels of opposing electrical change it is possible to modify the solubility characteristics of the resulting mixture and to control the rate of release of medicament from this matrix, by solubilisation of at least one component by the amylolytic enzyme present in saliva.

The accompanying examples illustrate formulations which optimise the absorption of strongly lipophilic medicaments through the mucosae of the buccal and sublingual epithelia and result in the required pharmacokinetic profile for optimum therapeutic action. These formulations contain lipophilic medicaments either emulsified in a matrix or contained as an emulsifiable mass within an envelope covering the matrix. The matrix contains at least one self-emulsifying component that in contact with saliva forms a viscous emulsion which adheres reversibly to the mucous membrane, without causing irritation or damage, or stimulating excessive salvation. When the dosage form is introduced into the mandibular or maxillary fossae, or placed under the tongue it hydrates and adheres to the mucosae. The hydrated, emulsified mass so formed remains in contact with a large area of he buccal and sublingual mucosae, and releases medicament over a period of 0.1–60 minutes (preferably 0.5–15 minutes). Table 2 lists pharmaceutically acceptable excipients and types of excipient which can be included (without limitation of the invention) to give a suitable degree of viscosity when the dose unit is placed in contact with saliva. The dosage form may formed by fusion or compression into a mold sealable to exclude light and air.

Where medicaments are soluble in water it is possible to disperse the medicament over the epithelium of the buccal cavity and the sublingual mucosal. Provided that the medicament molecule (if ionised) has the appropriate ionisation constant, it will pass through the epithelium and be absorbed into the systemic circulation. Uncharged, lipid molecules will only pass into, and through, the oropharyngeal mucosae if they are brought into intimate contact with the mucosae.

Where medicaments are water insoluble, dispersion of oily materials in the aqueous environment of the mouth is uneven. When oily medicaments are brought into intimate contact with the mucosae there is an opportunity for absorption through the epithelium. However, oily substances have an unpleasant mouth feel generally, and it is necessary to formulate them in order to overcome this problem. Emulsions have a mouthfeel which is more acceptable than oil to most patients. Compliance (i.e. temporary abstinence from swallowing) is therefore improved.

Cannabinoids, the active constituents of cannabis, are soluble in highly non-polar solvents (i.e. in substances such as chloroform, dichloromethane and high concentrations of alcohol); they also have limited solubility in glycols. Some of these solvents are pharmaceutically unacceptable, and the pharmaceutically acceptable solvents need to be used in high concentrations to produce solutions which can be applied to the oral mucosae. Solubility in some of these solvents imposes a ceiling on the dose which can be given using conventional pharmaceutical methods of formulation.

In order to be absorbed from the sublingual/buccal mucosae it is essential that the cannabinoid is brought into intimate contact with the surface of mucosal cells. To this extent the formulation must be "wettable". Tetrahydrocannabinol (THC) is an oily liquid at room temperature; cannabidiol is an oil soluble solid. Both have very low solubility in aqueous excipients.

By direct experiment it has been discovered that formulation of a cannabinoid in a matrix which contains at least one self-emulsifying surfactant, surprisingly results in the generation of an oil in water (o/w) emulsion in a few seconds, i.e. as soon as the product is wetted by saliva. Viscolising agents with adhesive properties may be added to the formulation to ensure that the emulsion so formed adheres to the epithelium of the buccal cavity. Carbohydrate-based viscolisers are degraded by amylolytic enzymes in saliva and a combination of viscolisers can be devised such that there is progressive reduction in viscosity with dwell time in the buccal cavity. Advantage can also be taken of the solubilising effect of certain glycols and sugar alcohols which enhance the solubility of cannabinoids. Sugars, which are rapidly soluble, speed dissolution. Where it is necessary to use non-cariogenic solubilisers, sugar alcohols are used preferentially.

The principles of formulation suitable for administration of cannabinoids can also be applied to other medicaments such as alkaloids, bases and acids. The requirements are that, if the medicament is insoluble in saliva, it should be solubilised and/or brought into the appropriate unionised form by addition of buffering salts and pH adjustment (Table 2).

The invention will be further understood with reference to the following examples, together with the accompanying Figures in which:

FIG. 1 schematically illustrates the packaging of a dosage form according to the invention.

Figure 2:
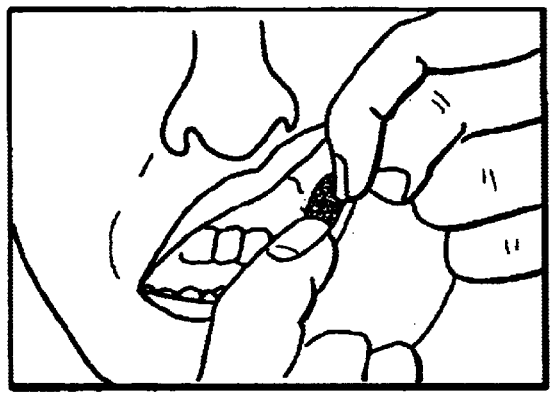

FIG. 2 schematically illustrates the application of a dosage form according to the invention to the maxillary fossa.

Figure 3:
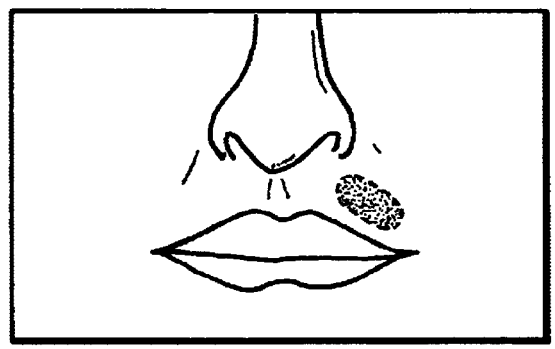

FIG. 3 schematically illustrates the dosage form in place.

Figure 4:
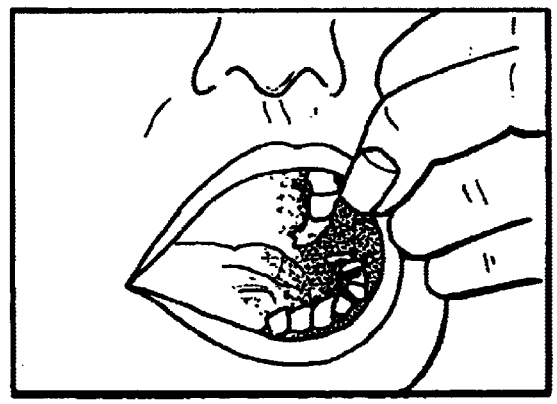

FIG. 4 schematically illustrates typical staining of the mucosa which would be observed after the dosage form as been in place for a period of 1 minute.

EXAMPLE 1

A 10% solution of pre-gelatinised starch (Component A) is made by dispersing one part of powdered pre-gelatinised starch in 9 parts of water, heating until gelatinised and then cooling. Pre-gelatinised cornstarch is the subject of a monograph in the US National Formulary. This product is used as a component of other formulations given in later examples, and is referred to as "starch gel". It has a negative surface charge.

EXAMPLE 2

There follows a description of the preparation of a formulation according to the invention in which hop extract, which is an oily resinous material, is used as the active ingredient. It has a bitter taste and this allows the patient to discern immediately when the active ingredient has stimulated the taste buds, and by implication has interacted with the mucosae. The dispersion of the formulation over the buccal and sublingual mucosae is revealed by the spread of colour. Any increased desire on the part of the patient to swallow the formulation can also be measured by direct observation.

In this example, a formulation is made by bringing together a gel (containing at least one active component which has a negative surface charge) together with a gel of opposing surface charge. The gel of opposing surface charge may contain optionally at least one active component which may be the same as that in the gel of opposite charge or another active ingredient. When the gels of opposing surface charge are brought together coacervation occurs resulting in a change in viscosity although the resulting gel is still thermoplastic and capable of being dispensed into molds. On cooling the gel sets into a flexible but rigid gel.

Glycogelatin is prepared by heating bovine or porcine gelatine, or fish gelatine (isinglass) 18 parts and glycerol 2 parts on a water bath with distilled water sufficient to produce a final weight of 100 parts by weight. The glycogelatin so produced is a clear, rigid gel which surprisingly is inherently stable. It is resistant to microbial attack and is in equilibrium with air at a relative humidity of 60–70%.

A composition is prepared from:

| | |
|---|---|
| Glycerl monostearate | 5 parts |
| Soy lecithin | 7 parts |
| Chlorophyll (oil-soluble) | 3 parts |
| Component A | 30 parts |
| a-Tocopherol BP | 0.1 part |
| Extract of hops | 10 parts |
| Glycogelatin to produce | 100 parts |

The mixture is heated, with stirring to a temperature of 90° C. (using a water bath or in a microwave oven). The mixture is thoroughly stirred and while still molten 2 g aliquots are dispensed into aluminium foil molds which have been treated with a releasing agent. A range of releasing agents is suitable for this purpose; a solution of silicone or beeswax in normal hexane is sprayed onto the concave mold, and he solvent allowed to evaporate. The weight of finished product can be varied to accommodate quantities of cannabis extract up to approximately 250 mg per piece representing a content of approximately 150 mg of THC or CBD.

When cool, a foil laminate is placed over the mold and sealed by the application of heat. Evacuation of air and replacement with nitrogen is carried out before final sealing so that the small, residual space in the finished dose unit is an inert, non-oxidising atmosphere.

The product so formed is a lenticular ovate gel which has one convex surface and one plain surface. It contains a colouring agent which is oil soluble and indicates the pattern of distribution of emulsion over the buccal cavity. Incorporation of chlorophyll as a disclosing agent is an optional feature; where used it indicates the areas of buccal mucosae to which a product containing medicament would also spread. These features of the invention are illustrated in FIGS. 1–4. It will be clear to a person skilled in the art that variations in the emulsifiers and the physical shape and form of packaging are within the teaching of the invention.

EXAMPLE 3

The formulation described above produces a product which is an elastic but rigid gel. When half of the tablet is placed between the upper jaw and the inside of the mouth (maxillary fossa) on either side, it starts to melt within one minute and at two minutes has produced an emulsified mass which covers the buccal mucosae. The gel does not produce a discernible sensation when placed between the maxilla and buccal mucosae, and does not induce a desire on the part of the subject to swallow the preparation. The area of buccal mucosae which is covered can be demonstrated by a photographic record taken before, one minute, two minutes, five minutes and 10 minutes, or other convenient time interval after the dosing.

The formulation has a slight taste characteristic of chlorophyll and extract of hops which was discernible for us to 10 minutes after placing the gel in situ.

The distribution of colour (within one minute, and the persistence of taste for up to 10 minutes) indicates that this type of formulation is suitable as a vehicle for administration of highly lipid soluble medicaments such as cannabis extract or cannabinoids. As formulated, it can be used as, a self-indicating placebo preparation in clinical trials. The accompanying figures illustrate the distribution of one half of a product placed in the mouth. The configuration of the product, and the area of distribution of the product when emulsified in situ is shown in FIGS. 1–4. FIG. 3 shows the position in which the device is originally placed. For clarity of demonstration, the illustration shows the product placed on one side of the mouth. However, it may be divided and placed bilaterally to ensure maximal distribution. Alternatively, products containing different active ingredients can be placed simultaneously, but on separate sides of the mouth.

EXAMPLE 4

The device described in Example 1 is clamped between two pieces of nylon mesh and attached to the basket of a BP design of tablet disintegration equipment at a temperature of 35° C. The gel disperses within 1–2 minutes to produce a fine even-textured emulsion.

EXAMPLE 5

This Example relates to the preparation of a dosage form containing a mixture of extracts of cannabis. The extracts of cannabis are referred to as Cannabis Based Medicine Extract (CBME) for ease of reference. An extract from a chemovar (variety) of cannabis producing more thin 90% of its total cannabinoid as cannabidiol (CBD) may be prepared by supercritical fluid extraction of dried cannabis herb. This is referred to as CBME-G5. Similarly, an extract with a high proportion (more than 95%) total cannabinoid as tetrahydrocannabinol (THC) is referred to as CBME-G1. The formula in this example can be varied to accommodate CBME with greater or lesser content of cannabinoids, in order to achieve the desired ratio of THC to CBD, and other cannabinoids. Products containing different ratios of THC to CBD are useful for treatment of specific therapentic conditions.

A mixture is produced by melting together the following ingredients:

| | |
|---|---|
| Glyceryl mono oleate | 10 parts |
| Soy lecithin | 10 parts |
| Curcumin | 0.1 part |
| Component A | 20 parts |
| CBME-G5 to give CBD | 1 part |
| CBME-G1 to give THC | 2 parts |
| α-Tocopherol | 0.1 part |
| Ascorbyl palmitate BP | 0.1 part |
| Glycogelatin to produce | 100 parts |

The components are mixed with gentle heat on a water bath, stirred and poured while hot into molds. The product in molds is finished as described in Example 1 and sealed under an atmosphere of inert gas.

In this formulation the curcumin imparts a bright yellow colour which allows the area of distribution of the product in the mouth to be identified. α-Tocopherol and ascorbyl, palmitate are antioxidants which together with glyceryl mono oleate provide an effective antioxidant system.

The relatively large size (1–2 g) of this dosage form allows a comparatively large amount of active ingredient to be incorporated in the dosage form. Cannabidiol may be given in doses of 900 mg/day and the dosage form described alloys this dose to be given in 2–9 (and preferably 2–4) divided doses per day.

Tetrahydrocannabinol is more active w/w than cannabidiol, and where a smaller unit dose of THC may be required it is possible to include this dose in a sublingual tablet of conventional size. Example 6 illustrates the formulation of such a tablet.

EXAMPLE 6

| | |
|---|---|
| Glyceryl monostearate (self emulsifying grade) | 5 parts |
| Polysorbate 80 | 0.5 parts |
| Lactose (direct compression grade) | 79.3 parts |
| Soluble starch | 10 parts |
| Tetrahydrocannabinol | 5 parts |
| Ascorbyl Palmitate | 0.1 part |
| α-Tocopherol | 0.1 part |
| Ethanol (dehydrated) BP | 10 parts |

The GMS, polysorbate, ascorbylpalmitate, a-Tocopherol and THC are dispersed and dissolved in the alcohol. The alcoholic solution is sprayed onto the dry powder ingredients which have been thoroughly mixed. Ethanol is allowed to evaporate and the granules are dusted with 1% of talc and compressed to a target tablet weigh of 101 mg in a conventional tablet press. Biconvex punches with a diameter of 7 mm or 9 mm produce tablets with a high surface/weight ratio. These absorb water when placed in contact with the sublingual or buccal mucosae. The rate of dissolution can be adjusted by altering the degree of compression. Tablets compressed to a pressure of 1–3 Newtons give tablets which disperse in a period of 0.5–5 minutes. The disintegration is determined by the method described in Example 4, and for these tablets was less than one minute.

EXAMPLE 7

The generation of an emulsion from a self-emulsifying matrix is not limited to solid dosage forms. In the following example a liquid formulation suitable for sublingual application is exemplified. A solution as produced by melting together (at a temperature not exceeding 50° C.) the following ingredients:

| | |
|---|---|
| Glyceryl monoleate (self-emulsifying) | 2 parts |
| Medium chain triglycerides | 5 parts |
| Cremophore RH40 | 30 parts |
| CBME-G1 to give THC | 10 parts |
| α-Tocopherol | 0.1 part |
| Ascorbyl palmitate | 0.1 part |
| Ethanol BP to produce | 100 parts |

The product formed by mixing these ingredients is dispensed in 10 ml quantities into a glass vial and closed with a pump action spray break-up button. Each 1 ml of product contains 100 mg of THC and each actuation of the pump delivers a fine spray which can be directed to the area of mucosae under the tongue.

Although solutions of CBME in ethanol alone can be used as a spray, the quantity of cannabinoid which can be delivered is limited by their solubility in ethanol alone. The aggressive nature of pure ethanol as a solvent, in turn, further limits the amount which can be applied to the mucosae without producing discomfort to the patient. Surprisingly, the addition of a self-emulsifying primary surfactant and solubiliser allows a greater quantity of cannabinoid to be contained in a unit dose. Spraying small quantities onto the sublingual mucosae results in evaporation of a significant amount of ethanol, and the emulsion so produced is non-irritant and does not stimulate the swallowing reflex. This provides greater dwell time for the in situ-formed emulsion to be in contact with the sublingual mucosae. A particular feature of this formulation is the accessory solvent activity of the medium chain triglycerides which also act as a secondary emulsifier.

EXAMPLE 8

The solid dosage form may be a soft gelatin capsule, which can be crushed to release the medicament to give an emulsion. The capsule can then be swallowed to provide the residue of the dose for absorption in the remainder so the gastrointestinal tract. The soft gelatin capsule provides an emulsified form of medicament which can be absorbed from any part of the GI tract. A capsule mass may be made from the following ingredients:

| | |
|---|---|
| Glyceryl monostearate (self emulsifying) | 5 parts |
| Polysorbate 80 | 1 part |
| Beeswax | 5 parts |
| CBME G1 to give THC | 10 parts |
| CBME G5 to give CBD | 10 parts |
| α-tocopherol | 0.1 part |
| Ascorbyl palmitate | 0.1 part |
| Hemp oil to produce | 100 parts by weight |

EXAMPLE 9

| | |
|---|---|
| Sorbitol | 35 parts |
| Gum Acacia | 20 parts |
| Glyceryl Mono-oleate (GMO) | 10 parts |
| Egg lecithin | 10 parts |
| CBME-1 to produce 5 mg THC | 5 parts |
| CBME-5 to produce 5 mg CBD | 5 parts |
| Tocopherol | 0.1 parts |
| Ascorbyl palmitate | 0.1 parts |
| Vanillin | 0.1 parts |
| BHT | 0.01 parts |
| Glycerol | 5.0 parts |
| Water | qs |

The fat soluble ingredients are melted together at a temperature of 70° C. Sorbitol is mixed with the Acacia gum, dispersed in glycerol, and added to the other solid ingredients. Water is added, and the mass heated on a boiling water bath until evenly dispersed/dissolved. While still at a temperature of 60° C. the mass is distributed into molds (as described in Example 1). The mass can also be cast or rolled into a sheet, preferably 2.5 mm thick. Oval or hexagon-shaped pieces with an area of 40 mm$^2$ are cut and the pieces applied to a non-stick backing sheet larger than the piece, and covered with a non adhesive protective membrane. The patch so formed is sealed under an inert gas blanket into a pocket formed from heat-sealable foil laminate. The product so produced is suitable for treatment of patients suffering from epilepsy, multiple sclerosis and other types of neuropathic and neurogenic pain, where it is necessary to have release of the medicament over a period of more than a few minutes.

EXAMPLE 10

A product providing fast release of a constituent and a further release of constituent over a prolonged time can be produced by making a combination dose unit. Using he formulation described in Example 8, a quantity of heated mass is filled into a mold or cast into a film, and allowed to set. A layer of material as described in Example 5 is then cast onto the surface of the gel described in Example 9. The composite gel is then packaged as described in these examples. Variation of the proportions of mass in the two layers provides for modification of the kinetic profile produced ban the dose unit.

In some circumstances it may be desirable to administer two drugs in a time dependent order. This can arise where one drug of the pair has a protective effect on the other. Example 10 describes a composite gel formulation of the type described in earlier examples. The formulation described in Example 11 provides CBD which is an antioxidant known to have a protective effect on THC to be made available for absorption through the buccal/sublingual mucosae just before THC. Cannabidiol is contained in the fast release layer and THC is dissolved out of the delayed release layer. Example 11 describes a dose unit consisting of two layers with differing dissolution characteristics.

EXAMPLE 11

| (a) | Glyceryl mono-oleate | 7 parts |
| --- | --- | --- |
|  | Soy lecithin | 7 parts |
|  | Acacia gum | 15 parts |
|  | Tetrahydrocannabinol | 10 parts |
|  | α-tocopherol | 0.1 parts |
|  | Xylitol | 5.1 parts |
|  | Glycerol | 3 parts |
|  | Purified Water to produce | 100 parts |

A molten mass is prepared as described in previous examples and aliquots cast into molds or as a sheet.

| (b) | Glycerol mono-oleate | 15 parts |
| --- | --- | --- |
|  | Soy lecithin | 10 parts |
|  | Component A | 20 parts |
|  | α-tocopherol | 0.1 parts |
|  | Cannabidiol | 20 parts |
|  | Glycogelatin to produce | 100 parts |

A mass is prepared as described in Example 2. The mass is cast as a second layer into a mold containing an aliquot of formulation (a). At the interface there is slight melting and bonding of the two components to give a coherent product. If the gel is cast into a concave mold, the product has a planar surface which, if placed in contact with the mucosa is the first to disperse and thus produces the required sequence or presentation of components for absorption.

A layer of formulation (b) can be cast on the surface of a sheet of formulation (a). The two formulations contain colloidal components with opposing signs and at the zone of fusion good adhesion is produced by conacervation. The composite layer is then cut into shapes suitable for application to the oral mucosae. The product is packed as described in Example 3 and protected from air and light.

TABLE 1

Examples of medicaments which can be included in formulations according to the invention.

| CLASS OF MEDICAMENT | EXAMPLE OF MEDICAMENT |
| --- | --- |
| Alkaloid-rich extracts of *Belladonna atropa* | Hyoscine |
|  | Hyoscymine |
|  | Atropine |
| Alkaloid-rich extracts of *Gallanthus spp.* |  |
| Alkaloid-rich extracts of *Narcissus spp.* |  |
| Alkaloid-rich extracts of opium | Morphine |
|  | Codeine |
|  | Diamorphine |
| Alkaloid-rich extracts of Pilocarpine | Pilocarpine salycilate |
| Anti-asthmatics | Terbutaline |
| Antibacterials |  |
| Antifungals | Fluconazole |
| Anti-inflammatory agents | Benzidamine |
|  | Pyroxicam |
| Antivirals | Acyclovir |
|  | Zidovudine |
| Beclomethasone |  |
| Cannabinoid-rich fractions of *Cannabis sativa* and *Cannabis indica*, and chemovars derived from them |  |
| Cannabinoids | $\Delta^{-9}$ Tetrahydrocannabinol (THC) |
|  | Cannabidiol (CBD) |
|  | Cannabinol (CBN) |
| Cannbinoid-rich fractions containing cannabinoids other than THC, CBD or CBN as the most abundant component |  |
| Cardiovascular Agents | Nifedipine |
|  | Diltiazem |
|  | Verapamil |
| Centrally acting analgosics | Butorphenol |
|  | Buprenorphine |
|  | Fentanyl |
| Fluticasone proprionate |  |
| Polyunsaturated fatty acid triglycerides | n-3 and n-6 PUFAs |
|  | Acylglycerols |
| Sympathomimetic aminos | Salbutamol |

Classes of compound are indicated in bold. Examples of compounds are intended to be illustrative rather than limiting to the invention. The person skilled in the art will appreciate that compounds having a unit dose less than 10 mg are most conveniently given in the form of small tablets as described in Example 6. Compounds where the unit dose is greater are most conveniently included in the gel formulations which can accommodate higher unit doses of medicament.

agent when hydrated forming an emulsion containing said THC and CBD which is capable of adhering reversibly to a mucosal surface and allowing controlled release of the THC and CBD.

2. A pharmaceutical formulation according to claim 1, wherein said agent which is both a self emulsifier and a cannabinoid solubilizer is selected from the group consisting of glycerol monooleate, glycerol monostearate, medium chain triglycerides, polyethoxylated caster oil, polyoxyeth-

TABLE 2

Classes of compound and examples of agents which can be used to produce emulsification, mucoadhesion and an increase in viscosity. The designation as primary (1°) or secondary (2°) emulsifier is for convenience. Many of the agents can be used alone or in combination to fulfil the role of primary or secondary emulsifier.

| Compound Class/Example | Preferred Quantity % w/w | Surface Charge (where known) | Regulatory Approval | Comments |
|---|---|---|---|---|
| Acacia | | Negative | M | Forms a viscous coacervate with positively charged gels such as gelatin |
| Alcohols | | | | |
| Celostearyl | 1–20 | | F,M | 2° emulsifier |
| Cetyl | 1–15 | | | 2° emulsifier |
| Anionic emulsifying wax | 3–30 | | M | 1° self emulsifier |
| Cellulose, hydroxypropyl | 5–35 | | G,F,M,R | 2° emulsifier, stabiliser, viscoliser |
| Diethanolamine (DEA) | 1–10 | | M,F,R | 1° self emulsifier |
| Gelatin | 40–70 | Positive | F,M | Gelling agent |
| Glyceryl monoleate | 1–30 | | G,F,R | 1° self emulsifier, solubiliser |
| Glyceryl monostearate | 2–20 | | G,M,F,R | 1° self emulsifier, solubiliser, tablet lubricant |
| Lecithin | 2–15 | | G,M,F,R | 2° emulsifier |
| Medium Chain Triglycerides | 1–10 | | G,R | 2° emulsifier, solvent |
| Methylcellulose | 1–5 | | G,M,F,R | 2° emulsifier, viscoliser |
| Nonionic emulsifying wax | 5–25 | | M,R | 1° emulsifier, viscoliser |
| Poloxamer | 2–10 | | M,F,R | 2° emulsifier, viscoliser |
| Polydextrose | | Negative | | Viscoliser |
| Polyethoxylated Castor Oil | 1–10 | | M,F,R | 1° self emulsifier, solubiliser, stabiliser |
| Polyoxyethylene alkyl ethers | 10–20 | | M,R | 1° self emulsifier, solubiliser |
| Polyoxyethylene ethers (Macrogols) | 1–15 | | M,R | 1° self emulsifier, solubiliser, wetting agent |
| Polyoxyethylene fatty acid esters (polysorbates) | 0.5–10 | | G,M,F,R | 1° self emulsifier, solubiliser |
| Polyoxyethelene stearates | 0.5–10 | | M,F,R | 2° emulsifier, solubiliser |
| Pregelatinised starch | 1–20 | Negative | G,F,R | Coacervates with gelatin, viscolisers |
| Propylene glycol alginate | 1–5 | | G,M,F,R | 2° emulsifier, viscoliser |
| Sodium lauryl sulfate | 0.5–2.5 | | G,M,F,R | 1° self emulsifier |
| Sorbitan esters (sorbitan fatty acid esters) | 0.1–15 | | Food, M,F,R | 1° self emulsifier, solubiliser |
| Starch | 2–15 | Negative | G,M,F,R | Viscoliser, tablet diluent, disintegrant |
| Tri-sodium citrate | 0.3–4 | | G,M,F,R | 2° emulsifier, pH modifier, sequestering agent |

M - Monograph in major pharmacopoeias
F - Accepted in FDA Inactive Ingredients Guide
R - Included in parenteral medicines, licensed in the UK or Europe
G - Generally Regarded as Safe

What is claimed is:

1. A pharmaceutical formulation for use in administration of cannabinoids via a mucosal surface, the formulation comprising tetrahydrocannabinol (THC) and cannabidiol (CBD) and a matrix comprising at least one agent which is both a self-emulsifier and a cannabinoid solubilizer, said agent when hydrated forming an emulsion containing said ylene alkyl ethers, polyoxyethylene ethers, polyoxyetyhlene fatty acid eaters, polyoxyothylene stoarates and sorbitan esters.

3. A pharmaceutical formulation according to claim 2, wherein said agent which is both a self-emulsifier and a cannabinoid solubilizer is polyoxyethylene caster oil.

4. A pharmaceutical formulation according to claim 2, wherein said agent which is both a self-emulsifier and a cannabinoid solubilizer is a cremophore.

5. A pharmaceutical formulation according to claim 2, which includes ethanol, wherein said agent which is both a self-emulsifier and a cannabinoid solubilizer is a cremophore.

6. A pharmaceutical formulation according to claim 1, wherein the ratio of THC to CBD is selected from the group consisting of: a ratio of THC:CBD of 2:1, a ratio of THC:CBD of 1:1 and a ratio of THC:CBD of 1:2.

7. A pharmaceutical formulation according to claim 1, wherein the matrix further comprises one or more viscolising agents.

8. A pharmaceutical formulation according to claim 7, wherein the matrix comprises at least on viscolising agent that when hydrated forms a gel having positive surface electrical charge and at least one viscolising agent that when hydrated forms a gel having negative surface electrical charge.

9. A pharmaceutical formulation according to claim 7, wherein at least one of the viscolising agents is solubilized by the action of an enzyme present in saliva.

10. A pharmaceutical formulation according to claim 7, wherein the viscolising agent is a carbohydrate.

11. A pharmaceutical formulation according to claim 7, wherein the viscolising agent is starch.

12. A pharmaceutical formulation according to claim 1 which is in the form of a gel, a compressed tablet, a liquid or a capsule.

13. A pharmaceutical formulation according to claim 1 which is in the form of a gel for administration of one or more cannabinoids via the sublingual and/or buccal mucosae, wherein on contact with saliva the gel forms an emulsion containing said at least one cannabis extract that adheres reversibly to the sublingual and/or buccal mucosae.

14. A pharmaceutical formulation according to claim 1, which includes at least one cannabis extract.

15. A pharmaceutical formulation for use in administration of at least one cannabis extract "containing the cannabinoids tetrahydrocannabinol (THC) and cannabidiol (CBD)" via a mucosal surface, the formulation comprising said at least one cannabis extract and a matrix comprising at least one agent which is both a self-emulsifier and a cannabinoid solubilizer, said agent when hydrated forming an emulsion containing said at least one cannabis extract "containing the cannabinoids tetrahydrocannabinol (THC) and cannabidiol (CBD)" which is capable of adhering reversibly to a mucosal surface and allowing controlled release of the cannabinoids from said extract "containing the cannabinoids tetrahydrocannabinol (THC) and cannabidiol (CBD)".

16. A pharmaceutical formulation according to claim 15 wherein said agent which is both a self-emulsifier and a cannabinoid solubilizer is selected from the group consisting of glycerol monooleate, glycerol monostearate, medium chain triglycerides, polyethoxylated caster oil, polyoxyethylene alkyl ethers, polyoxyethylene ethers, polyoxyethylene fatty acid esters, polyoxyethylene stearates and sorbitan esters.

* * * * *

UNITED STATES PATENT AND TRADEMARK OFFICE
CERTIFICATE OF CORRECTION

PATENT NO. : 6,730,330 B2
DATED : May 4, 2004
INVENTOR(S) : Whittle et al.

It is certified that error appears in the above-identified patent and that said Letters Patent is hereby corrected as shown below:

Column 14,
Lines 9-21, replace claim 15, with the folowing:

-- A pharmaceutical formulation for use in administration of at least one cannabis extract containing the cannabinoids tetrahydrocannabinol (THC) and cannabidiol (CBD) via a mucosal surface, the formulation comprising said at least one cannabis extract containing the cannabinoids tetrahydrocannabinol (THC) and cannabidiol (CBD) and a matrix comprising at least one agent which is both a self-emulsifier and a cannabinoid solubilizer, said agent when hydrated forming an emulsion containing said at least one cannabis extract containing the cannabinoids tetrahydricannabinol (THC) and cannabidiol (CBD) which is capable of adhering reversibly to a mucosal surface and allowing controlled release of the cannabinoids from said extract containing the cannabinoids tetrahydrocannabinol (THC) and cannabidiol (CBD). --

Signed and Sealed this

Fifth Day October, 2004

JON W. DUDAS
*Director of the United States Patent and Trademark Office*